US006383393B1

(12) United States Patent
Colpan et al.

(10) Patent No.: US 6,383,393 B1
(45) Date of Patent: May 7, 2002

(54) CHROMATOGRAPHIC PURIFICATION AND SEPARATION PROCESS FOR MIXTURES OF NUCLEIC ACIDS

(75) Inventors: Metin Colpan, Essen; Joachim Schorr; Ralf Herrmann, both of Dusseldorf; Petra Feuser, Cologne, all of (DE)

(73) Assignee: Qiagen GmbH, Hilden (DE)

( * ) Notice: Subject to any disclaimer, the term of this patent is extended or adjusted under 35 U.S.C. 154(b) by 0 days.

(21) Appl. No.: 08/392,882
(22) PCT Filed: Jun. 24, 1994
(86) PCT No.: PCT/EP94/02056
§ 371 Date: Mar. 15, 1996
§ 102(e) Date: Mar. 15, 1996
(87) PCT Pub. No.: WO95/01359
PCT Pub. Date: Jan. 12, 1995

(30) Foreign Application Priority Data

Jul. 1, 1993 (DE) .......................................... 43 21 904

(51) Int. Cl.[7] .............................................. B01D 15/08
(52) U.S. Cl. .................... 210/656; 210/198.2; 536/25.4
(58) Field of Search ............................. 210/198.2, 635, 210/636; 536/23.1, 25.4; 435/270

(56) References Cited

U.S. PATENT DOCUMENTS

| 5,057,426 A | * 10/1991 | Henco et al. ................ 435/270 |
| 5,075,430 A | * 12/1991 | Little .......................... 536/27 |
| 5,155,018 A | * 10/1992 | Gillespie et al. .............. 435/91 |
| 5,187,083 A | * 2/1993 | Mullis .......................... 435/91 |

FOREIGN PATENT DOCUMENTS

| EP | 0389063 | * | 9/1990 |
| WO | 93/11221 | * | 6/1993 |

OTHER PUBLICATIONS

Snyder et al. Introduction to Modern Liquid Chromatography, 2nd ed. pp. 281–289, 1979.*

* cited by examiner

Primary Examiner—Ernest G. Therkorn
(74) Attorney, Agent, or Firm—Jacobson Holman, PLLC

(57) ABSTRACT

A method for the purification and separation of nucleic acid mixtures by chromatography including adsorbing the nucleic acids to be separated and purified from a solution with a high concentration of salts (ionic strength) and/or a high concentration of alcohol on a substrate and subsequent desorbing from the substrate by means of a solution with lower concentration of salts (ionic strength).

23 Claims, No Drawings

CHROMATOGRAPHIC PURIFICATION AND SEPARATION PROCESS FOR MIXTURES OF NUCLEIC ACIDS

The object of the present invention is a method for the purification and separation of nucleic acid mixtures by chromatography, the use of said method for purifying nucleic acid fragments that have been subjected to modification reactions, a device for performing said method, an aqueous solution which can be used in the method according to the invention, and the use of said solution.

Adsorbing nucleic acids on glass or silica-gel particles in the presence of chaotropic salts is well-known (Vogelstein, B. and Gillespie, D.(1979); Preparative and analytical purification of DNA from agarose, Proc. Natl. Acad. Sci. USA 76: 615–619). According to this method, using high concentrations of chaotropic salts, such as sodium iodide, sodium perchlorate, or guanidine thiocyanate, DNA is isolated and purified from agarose gels and RNA and DNA preparations are isolated and purified from various extracts (Boom, R. et al. (1990); Rapid and simple method for purification of nucleic acids, J. Clin. Microbiol. 28, 495–503, and Yamado, O. et al. (1990); A new method for extracting DNA or RNA for polymerase chain reaction, J. Virol. Methods 27, 203–210). Although the physical processes resulting in an adsorption of the nucleic acids on mineral substrates in the presence of chaotropic reagents are not understood in detail, it is believed that the reason of this adsorption dwells in disturbances of higher-order structures of the aqueous medium. This leads to adsorption or denaturation of the dissolved nucleic acid on the surface of the glass or silica-gel particles. In the presence of high concentrations of chaotropic salts, this adsorption will occur almost quantitatively. Elution of the adsorbed nucleic acids is performed in the presence of buffers having low ionic strengths (salt concentrations). The prior art methods allow for the treatment of nucleic acids and fragments ranging in size from 100 base pairs (bp) to 50,000 base pairs (bp). To date, it has not been possible, however, to quantitatively separate short single-stranded or double-stranded nucleic acid fragments (100 bp and smaller) from very short (20 to 40 nucleotides) single-stranded oligonucleotides (e.g. primers).

Typically, such nucleic acid mixtures are formed as amplification products, for instance by polymerase chain reaction (PCR). In many cases, the products resulting from this reaction are subsequently analyzed in terms of molecular biology, using the conventional techniques such as DNA sequencing, DNA hybridization, cloning, restriction enzyme analysis, and transformation. Thereby, analytical parameters, such as information about genetic mutations for genetic advising or detection of pathogens in medical diagnostics (e.g. HIV), can be obtained. To be capable of making full use of the potential of those diagnostic methods, quantitative separation or purification of these DNA fragments which are often quite small (100 base pairs) is very important.

Presently available purification methods are based on ultrafiltration, high pressure liquid chromatography (HPLC), or extraction of nucleic acid fragments from agarose gels in the presence of chaotropic salts by precipitaion onto glass or silica-gel particles. For the separation of nucleic acid mixtures comprising for example a double-stranded DNA fragment (100 bp) and a smaller single-stranded oligonucleotide (for instance 39-mer), however, these methods are useful only with low efficiency.

The technical problem of the present invention consists in providing a method allowing to avoid the above-mentioned drawbacks of the prior art. This problem is solved by a method for the purification and separation of nucleic acid mixtures by chromatography according to the features described herein.

An embodiment of the invention pertains to the use of the method according to the invention for the purification of nucleic acid fragments following modification reactions, a device for performing the method according to the invention, and an aqueous solution that can be used in the method according to the invention, and a combination of the device and the aqueous solution.

The method according to the invention makes use of the per se known property of nucleic acids to precipitate onto mineral substrates in the presence of chaotropic salts, solutions of salts having high ionic strengths (high concentrations), reagents such as e.g. urea, or mixtures of such substances and to be eluted by the action of solutions of low ionic strengths (salt concentrations). Thus, Applicant's PCT/EP 92/02775 suggests to first adsorb a nucleic acid mixture contained in a medium of low ionic strength on an anion-exchanging material, to subsequently desorb the nucleic acid by means of a buffer of higher ionic strength and then to adsorb the nucleic acids contained in the buffer of this higher ionic strength on a mineral substrate material in the presence of lower alcohols and/or polyethylene glycol and/or organic acids, such as trichloroacetic acid (TCA). Thereafter, the nucleic acids are eluted preferably by means of water or a buffer solution of low ionic strength.

It has now been found that for the separation of nucleic acids, preliminary purification on anion-exchanging materials can be dispensed with. Surprisingly, excellent fractioning of a nucleic acid mixture can also be accomplished by adsorbing the nucleic acids in the presence of high concentrations of chaotropic salts and desorbing the nucleic acids by means of solutions of low ionic strengths.

Thus, the method according to the invention allows for efficiently obtaining nucleic acid fractions of interest in one operation step without preliminary purification steps by adsorbing the nucleic acids to be separated and eluting them.

If samples containing nucleic acids are to serve as sources of the nucleic acids to be purified and isolated, those sources are digested in a per se known manner, for example by treatment with detergents or by mechanical action, such as ultrasonic waves or disintegration. The solution used to receive the nucleic acids may already contain high concentrations of chaotropic salts. After larger cell constituents that may be present have been removed by centrifugation or filtration (WO 93/11218 and WO 93/11211), the solution is contacted with a mineral substrate material in order to adsorb the nucleic acids from the solution having high ionic strength of chaotropic salts on the mineral substrate.

A modification of the method according to the invention consists in performing digestion of the nucleic acids directly within the buffer system employed for the adsorption. In this case, a particularly favorable nucleic acid distribution can be obtained.

Nucleic acids are commonly obtained from eukaryotic and/or prokaryotic cells (including protozoans and fungi) and/or from viruses. For example, the cells and/or viruses are digested under highly denaturing and, if appropriate, reducing conditions (Maniatis, T., Fritsch, E. F., and Sambrook, S., 1982, Molecular Cloning Laboratory Manual, Cold Spring Harbor University Press, Cold Spring Harbor).

One particular embodiment of the invention is especially useful for the isolation of plasmid or cosmid DNA from *E. coli*. Following lysis of the *E. coli* cells with sodium hydroxide/SDS, the solution is neutralized with potassium acetate (KAc, 0.2–0.9 M).

Normally, the cell lysate is neutralized after SDS lysis by means of 3 M potassium acetate. Then, in order to centrifuge off the cell fragments, 5 M guanidine hydrochloride or another high concentration solution of chaotropic salt is added to the cell lysate. With *E. coli* minipreparations, this will yield about 2–3 ml of the sample to be adsorbed on silica gel which is unfavorable, however, since it will have to be centrifuged off then which takes several hours.

After lysis with sodium hydroxide/SDS, the method according to the invention uses e.g. solutions of salts preferably containing

| | |
|---|---|
| 0.2 M KAc | / 5.5 M GuHCl, |
| 0.2 M KAc | / 5.5 M GITC, |
| 0.2 M NaAc | / 6 M NaClO$_4$, |
| 0.2 M NaAc | / 6 M GuHCl, or |
| 0.2 M NH$_4$Ac | / 6 M NaClO$_4$. |

Thereby, neutralization of the cell lysate and concurrent adjustment of the sample to high salt concentration conditions in silica gel is achieved resulting in substantial facilitation of work in everyday practice. Surprisingly, it has further been found that adsorption of nucleic acids on silica gel will also take place in the presence of anionic or cationic or neutral detergents, such as e.g. SDS, NP40, Tween 20, Triton X-100, CTAB, in combination with chaotropic salts, or that the presence of these detergents will even increase the DNA yield.

Widely used is the lysis of cells by means of detergents as denaturing reagents and degradation by particular enzymes of the protein structures and nucleic acid cleaving enzymes. Thus, sodium dodecylsulfate (SDS) and EDTA, for instance, are used as denaturing agents and proteinase K is used to degrade proteins. In most cases, the result of such lysing procedure is a highly viscous jelly-like structure from which the nucleic acids are isolated by phenol extraction, wherein long portions of the nucleic acids remain intact. After dialysis and precipitation, the nucleic acids are removed from the aqueous phase. This lysing procedure is such aggressive towards non-nucleic acid structures that pieces of tissue may also be subjected to it.

Due to this labor-intensive technique involving repeated change of reaction vessels, however, this method is unfavorable with large amounts of samples and routine preparations. Although this method can be automated, a commercially available device of this kind presently will manage about 8 samples at a time within four hours (Applied Biosystems A 371). Thus, this method is expensive and unsuitable for passing large series of samples. Another drawback is that subsequent reactions such as enzymatic amplification are adversely affected due to the large lengths of the isolated nucleic acids. In addition, the solutions obtained are highly viscous and difficult to handle. In particular, DNA of very large length rather is obtrusive since nucleic acids obtained by the prior art method have to be cleaved in a separate step to be further processed.

Although digestion of eukaryotic and/or prokaryotic cells and/or viruses in alkaline medium in the presence of detergents is technically simple, it also yields nucleic acids of large lengths which are unfavorable as described above.

The rough preparation of the nucleic acids is followed by subsequent reactions. Those subsequent reactions require a certain quality of nucleic acids. For instance, said nucleic acids must be largely intact, the yield of the preparation must be high and reproducible, and in addition, the nucleic acids must be present in high purity, devoid of proteins and cellular metabolites. The preparation route must be simple and economic and allow for automation. The preparation of the nucleic acids must be possible without the risk of cross-contamination with other samples, especially when enzymatic amplification reactions are used, such as polymerase chain reaction (PCR) (Saiki, R., Gelfand, D. H., Stoffel, S., Scharf, S. J., Higuchi, R., Horn, G. T., Mullis, K. B., and Ehrlich, H. A. (1988), Science 239, 487–491) and ligase chain reaction (LCR) (EP-A-88 311 741.8). For those subsequent reactions, it is desirable to obtain the nucleic acids in not too large chain lengths, to lyse the cells quantitatively, if possible, and in addition to avoid the above-mentioned drawbacks of the digestion methods known in the prior art.

Hence, it is desirable that a method allow for the isolation and concentration of nucleic acids from intact eukaryotic and/or prokaryotic cells and/or viruses or from body fluids. In particular, the nucleic acid thus obtained should be characterized by not too large chain lengths, be isolatable in a few steps and be capable of being directly subjected to the required subsequent reactions.

The modification, set forth above, of the method according to the invention allowing for this consists in lysing the sources of the nucleic acids, such as eukaryotic and/or prokaryotic cells and/or viruses.

Said digestion of nucleic acid containing sources, such as eukaryotic and/or prokaryotic cells and/or viruses, may preferably be performed by physical or chemical action. Lysis may be accomplished either mechanically, such as by ultrasonic waves or by osmotic shock, or chemically by means of detergents and/or chaotropic agents and/or organic solvents (e.g. phenol, chloroform, ether) or by alkaline digestion.

This procedure results in the preparation of nucleic acids with high purity and allows to perform qualitatively and quantitatively reproducible analytics, especially in combination with enzymatic methods for the amplification of nucleic acids. Digestion methods using detergents and/or chaotropic agents, concentrated solutions of salts, reagents such as urea, mixtures of these substances, and/or organic solvents or physical digestion methods such as heating of a sample have proven to facilitate subsequent applications. For instance, when the method according to the invention is used, shorter cellular DNA (<50 kb) or total nucleic acids from cells and/or viruses and/or body fluids are obtained. The purification method (i.e. the conditions while the nucleic acids are bound and eluted) results in fragmentation of the nucleic acids.

The combination of chaotropic agents with high ionic strengths and hydrophobic organic or inorganic polymers and/or alcohols and/or trichloroacetic acid (TCA) in the adsorption buffer ensures that in contrast to conventional purification methods the nucleic acids are quantitatively fixed with high specifity on the surface of the mineral substrate material, such as quartz fibers, following lysis and thus are protected from further nuclease attacking while contaminating components of the lysate will not bind. In this state of the nucleic acids being fixed, residual contaminating components are readily washed out, with subsequent elution of the pure nucleic acid in a smaller volume. Thus, reproducible average chain lengths of 20 to 40 kb are obtained. Under the conditions of digestion as described in examples 7 to 9, less than 10% are shorter than 10 kb. This represents an optimum length distribution for subsequent enzymatic nucleic acid amplification.

The special combination of salts, particularly chaotropic agents, and alcohols for the first time allows for concurrently isolating and purifying nucleic acids of a broad spectrum of chain lengths (10–100,000 base pairs).

The aqueous adsorption solution with a high concentration of salts contains 1 to 50% by volume of an aliphatic alcohol with a chain length of from 1 to 5 carbon atoms or polyethylene glycol.

Suitable mineral substrates are porous or non-porous materials based on metal oxides and mixed metal oxides, such as those made of silica gel, materials principally consisting of glass, alumina, zeolites, titanium dioxide, zirconium dioxide. Zeolites in particular have proven to be suitable mineral substrates.

Optionally, the mineral substrate material having the nucleic acids adsorbed thereon may be washed with a solution which, due to a relatively high alcohol content, will prevent the nucleic acids from being desorbed.

Then, the adsorbed nucleic acids are eluted with a buffer of low salt concentration (ionic strength), and the nucleic acids or nucleic acid fractions obtained are collected.

Suitable chaotropic salts are sodium perchlorate, guanidine hydrochloride (GuHCl), guanidine isothiocyanate (GTC), potassium iodide in concentrations of from 1 to 8 M. Also useful are concentrated solutions of salts, >1 M NaCl, KCl, LiCl, etc., reagents such as urea (>1 M), and combinations of such components. The lower alcohols present in the solution of the chaotropic salts are methanol, ethanol, isopropanol, butanol, and pentanol in amounts of 1 to 50%, inasmuch as they are miscible with water within these ranges. The ethylene glycols which may be preferably used have molecular weights of from 1,000 to 100,000, particularly of from 6,000 to 8,000. Said polyethylene glycol may be added to the buffer having high ionic strength in amounts of from 1 to 30%.

The particle size of the mineral substrate materials preferably is from 0.1 $\mu$m to 1,000 $\mu$m. If porous mineral substrates, such as for instance porous silica gel, porous glass, porous alumina, zeolites, are used, the pore sizes preferably are from 2 to 1,000 nm. The substrate material can be present, for instance, in the form of loose fillings and be contacted with the solutions containing nucleic acids to be separated and purified.

Preferably, however, the porous and non-porous substrate materials are in the form of filter layers arranged in some hollow body provided with an inlet and an outlet. The filter layers either consist of directed (woven) or undirected fibers made of glass, quartz, ceramics, or other materials, such as minerals, or they consist of a membrane in which silica gel is incorporated.

The method according to the invention is excellently useful for the separation of nucleic acid mixtures, including in particular short-chain nucleic acids having only slightly different chain lengths. Thus, DNA fragments with a size of 100 bp, for example, can be separated from smaller single-stranded oligonucleotides, for instance a 39-mer. In this case, the yield in DNA is then increased by 60 to 70% as compared with other conventional purification methods, such as ultrafiltration, HPLC, or the use of chaotropic salts alone.

When the method according to the invention is employed in which the digestion of the sources containing nucleic acids is performed in the receptive (adsorption) buffer, preparation of nucleic acids with a definite nucleic acid length spectrum is possible.

The method according to the invention allows for processing nucleic acid mixtures of every origin whatever. Thus, nucleic acids from biological sources such as all kinds of tissues, body fluids, such as blood, fecal matter after appropriate sample priming, which at any rate comprises incorporation of the sample in a solution with a high concentration of salts, preferably a high concentration of chaotropic ions, can be obtained. Nucleic acids formed by chemical reactions, such as those obtained by polymerase chain reaction (PCR), or plasmid DNA, genomic DNA and RNA and/or nucleic acids derived from microorganisms can also be separated and purified according to the invention.

The method according to the invention may also include the use of so-called plasmid DNA minipreparations from *Escherichia coli* for subsequent cloning or sequencing; the method according to the invention is also useful for isolating DNA and/or RNA from whole blood, plasma, serum, tissues, cell cultures, bacteria, in particular *Mycobacterium tuberculosis*, viruses, such as cytomegalovirus (nucleic acid DNA), RNA viruses, such as HIV, hepatitis B, hepatitis C, hepatitis δ viruses. Oligonucleotides are also nucleic acids within the meaning of the method according to the invention. Furthermore, the nucleic acids may be derived from sequencing reactions or other comparable reactions. Preparation of DNA or RNA from whole blood is particularly useful for subsequent determination of HLA type. The method according to the invention is particularly useful for isolating nucleic acids from *Mycobacterium tuberculosis*. This involves the necessity of rather drastic digesting methods, with conventional isolation techniques yielding only unsatisfactory results.

A device which may be preferably used in the method according to the invention is a hollow body, especially of cylindrical shape, provided with an inlet and an outlet. In the vicinity of the outlet, seen in the direction of flow of the solution through the hollow body, the mineral substrate material on which the nucleic acids are to be adsorbed is located. A means which in a preferred embodiment consists of two polyethylene frits arranged one above the other leaving some space between them fixes the substrate material, which is located in said space between the polyethylene frits, within the lumen of the hollow body. The means for fixing the substrate material may also be a self-supporting membrane in which the substrate material is embedded. Attachment of the substrate material or of the means fixing the substrate material can be effected by frictional or tensional forces generated for instance by clamping said means within the hollow body and/or by fixing said means with a tension ring.

The pore size of said means, preferably polyethylene or polypropylene frits, must be large enough to allow the lysate components to pass through without obstruction. Preferably said means have pore sizes from 5 to 200 $\mu$m. This device for the first time allows for simple, rapid and reproducible isolation of nucleic acids even from highly viscous lysates with a very high protein content (e.g. blood lysates which have a very high content of hemoglobin).

In an especially preferred embodiment, the mineral substrate material is a reticular membrane made of silica-gel, glass or quartz fibers having pore sizes of <5 $\mu$m on which the liberated nucleic acids are adsorbed.

Another preferred embodiment is represented by a device in which the mineral substrate material is a particular inorganic polymer such as silica gel or quartz gel with particle sizes of from 1 to 50 $\mu$M.

Said hollow body may be a commercially available tube, for instance. Between the two means being tightly pressed in, for instance polyethylene frits having pore sizes of 50 to 200 $\mu$m, there is one or more layers of a membrane having pores with sizes ranging from 0.1 to 1 $\mu$m which membrane is made of silica, glass or quartz fibers or of silica gels. This membrane has a thickness of about 0.2 to 1.0 mm, especially of 0.6 mm.

The capacity of the membrane material is about 20 to 100 µg of DNA. Of course, by stacking such membranes on top of one another, the capacity for DNA may be increased. When there is only small mechanical strain, welding or sticking of the membrane edges to the device may also be considered in which case the stabilizing effect of said means may be dispensed with, such that the membrane will seal the hollow body without said means. The membrane may then be fixed within the hollow body by placing a tension ring.

It is also possible to fill small columns with the silica gel described being located between 2 polyethylene frits having pore sizes of 35 µm. Preferably, the top frit is selected to have larger pores (10–250 µm, especially 50 µm). Said columns are preferably charged with about 70 mg of silica gel corresponding to a filling level of 3 mm.

Also preferred is the use of the above-mentioned method in strips with 8 parallel preparation facilities each, in the microtiter plate format (96 facilities for almost simultaneous preparation), and/or in combination with a filtration step and/or desalting step (see Applicant's Patent Applications P 41 27276.5, P 41 39 664.2).

In a preferred embodiment of the device, a polyethylene frit with a thickness of 0.5 to 1.5 mm and pore sizes of about 10 µm is clamped into a centrifuge chromatographic column in the shape of an essentially cylindrical hollow body. On this frit, there is charged a layer, about twice as thick, of silica gel having particle sizes of about 10 to 15 µm and pore sizes of 40 to 120 Å which is sealed by a second frit that may be of the same kind as the first frit. Preferably, the silica-gel layer may be condensed by pressure between the frits.

Another embodiment of the chromatographic column comprises glass fiber fragments having lengths of 10 to 300 µm as a substrate material located between two polyethylene frits with pore sizes of about 50 µm. Other suitable substrate materials are glass fiber papers, quartz fiber papers, glass fiber fabrics and other mineral papers and fabrics.

Another preferred embodiment of the device comprises a membrane in the vicinity of the outlet having silica-gel particles embedded therein. In this case, the membrane which preferably is self-supporting especially may be fixed by means of a tension ring. As a silica-gel membrane, an Empore silica-gel membrane of the firm of 3M may be used to advantage. A silica-gel membrane consisting of silica gel and porous PVC may also be fixed within the lumen of the cylindrical hollow body, especially by means of a tension ring.

In a preferred embodiment of the method according to the invention, the described device in one of its embodiments, for example, is charged with the solution of the nucleic acid mixture to be separated. Then, the solution is passed through the mineral substrate by suction or centrifugation or some equivalent measure as well as combinations thereof. The nucleic acids are then adsorbed on the substrate material as long as the solution has high ionic strength (salt concentration).

The invention will be illustrated in more detail by means of the following examples.

EXAMPLE 1
Isolation of High Copy Plasmid DNA

E. coli cells from a 3 ml HB 101 culture and containing the pUC 18 plasmid are centrifuged off and resuspended in 0.25 ml of buffer P1 (10 mM Tris-HCl, pH 8, 100 µg/ml RNase A) and lysed by adding 0.25 ml of buffer P2 (0.2 M NaOH, 2% SDS). The sample is neutralized by adding 0.35 ml of buffer N3 (4.2 M guanidine hydrochloride, 0.9 M potassium acetate, pH 4.8) and is at the same time adjusted to a final concentration of 1.75 M GuHCl. This concentration ensures binding without requiring further steps. The lysed sample is centrifuged for 10 min in an Eppendorf minicentrifuge at 13,000 rpm in order to remove cell fragments and the precipitated SDS. The supernatant containing the plasmid DNA is immediately pipetted onto a centrifuge chromatographic column. This centrifuge chromatographic column is centrifuged in a 2 ml centrifuge tube and washed by renewed centrifugation of 0.5 ml of PB buffer (5 M guanidine hydrochloride, 30% isopropanol), in order to remove impurities and proteins. The centrifuge chromatographic column is washed salt-free once by centrifuging through 80% ethanol/water and subsequently is centrifuged for 30 to 60 sec to completely remove excess ethanol. For elution, 0.05–0.2 ml of elution buffer (10 mM tris/HCl, pH 8.5) are centrifuged through the centrifuge chromatographic column into a 1.5 ml centrifuge tube. The plasmid DNA is then present in concentrated form in a solution with a very low concentration of salts. The yield is 15 µg to 20 µg of plasmid DNA with an A260/A280 ratio of 1.75.

EXAMPLE 2
Isolation of High Copy Plasmid DNA from 5 ml Cultures

According to example 1, a cell lysate of a 5 ml pUC 18 plasmid/XL 1 Blue culture is prepared and centrifuged through a centrifuge chromatographic column containing a silica-gel filling and washed. The plasmid DNA is eluted with 0.1 ml of TE buffer (10 mM tris/HCl, pH 8.5, 1 mM EDTA) heated at 80° C. The yield is 15–20 µg of plasmid DNA with an A260/A280 ratio of 1.7.

EXAMPLE 3
Isolation of Low Copy Plasmid DNA

According to example 1, a cell lysate of a 5 ml pBR322 plasmid/XL 1 Blue culture is prepared and centrifuged through a centrifuge chromatographic column containing a glass or quartz fiber membrane and washed. The plasmid DNA is eluted with 0.1 ml of TE buffer (10 mM tris/HCl, pH 8.5, 1 mM EDTA) heated at 80° C. The yield is 5–10 µg of plasmid DNA with an A260/A280 ratio of 1.7.

EXAMPLE 4
Purification of Amplification Products

A 100 µl PCR amplification reaction is mixed with 500 µl of PB buffer (5 M GuHCl, 30% isopropanol); preliminary separation of the paraffin oil layer covering the reaction mixture is not necessary. This mixture is pipetted onto a centrifuge chromatographic column containing a silica-gel membrane and centrifuged in a 1.5 ml centrifuge tube. The centrifuge chromatographic column is washed almost salt-free by treatment with 80% EtOH/water. For elution, 50 µl of elution buffer (10 mM tris, pH 8.5) are centrifuged through the centrifuge chromatographic column into another centrifuge tube. The PCR product thus purified is free from primers, dNTPs, polymerase, and salts and can be employed, for example, directly in a sequencing reaction in an ABI sequencer using the "Cycle Sequencing" protocol.

EXAMPLE 5
Purification of DNA Following Restriction Reactions

1 µg of DNA is treated with a restriction endonuclease. This DNA restriction reaction is mixed with 500 µl of PB buffer according to example 4, and further processing is as in example 4. The DNA obtained after elution is free from restriction endonucleases and salts, and the 260/280 ratio is 1.8.

EXAMPLE 6
Purification of DNA Following Enzymatic Radioactive Labeling

1 μg of DNA are radiolabeled in presence of γ-$^{32}$P-ATP by means of oligolabeling procedure. The reaction mixture is treated as in example 4. Thereby, the labeled DNA is purified from non-incorporated dNTPs, γ-$^{32}$P-ATP, salts and Klenow polymerase and may directly be employed for hybridization reaction.

EXAMPLE 7
Preparation of Nucleic Acids from Blood

Total nucleic acids preparation from blood: To 200 μl of citrate, heparin or EDTA blood in a 1.5 ml PPN tube are added 200 μl of a 4–8 M solution of a chaotropic salt (guanidine hydrochloride (GuHCl), guanidine isothiocyanate (GTC), potassium iodide), optionally an organic solvent (phenol, chloroform, ether), and a 5–100% detergent (NP40; Tween 20, Triton X-100, SDS, CTAB). Then, 200–1000 μg of a protease is added, and the mixture is incubated for 10 min at 70° C. or for a longer period of time at lower temperatures (e.g. for 30 min at room temperature). In this step, efficient lysis of all eukaryotic and/or prokaryotic cells and/or viruses (with concomitant inactivation of infective pathogens) and denaturing and enzymatic degrading of proteins (with concomitant removal of the proteins bound to the nucleic acids) are taking place simultaneously. Adding 210 μl of a 95–100% alcohol (methanol, ethanol, n-propanol, isopropanol, PEG, secondary and tertiary, short-chain or long-chain alcohols) provides highly specific binding conditions for nucleic acids, and the lysate thus adjusted is transferred to the device. Then, the lysate is passed through the membrane or gel matrix by centrifuging or applying pressure, with reversible binding of the nucleic acids to the membrane fibers or gel particles. Impurities, such as proteins, heme, heparin, iron ions, metabolites, etc., are washed out with 0.7 ml of 100 mM NaCl, 10 mM tris/HCl, pH 7.5, 30–80% of a pure alcohol (methanol, ethanol, n-propanol, isopropanol, PEG, secondary and tertiary, short-chain or long-chain alcohols) or a mixture of alcohols. DNA is eluted either with a buffer with low concentration of salts (10 mM tris/HCl, pH 9.0) or with destined (deionized) water. The advantage of such elution procedures is that the DNA thus obtained may be directly used in subsequent reactions, especially PCR, without further precipitation or buffer-exchange steps. Preparation of nucleic acids from other body fluids, such as e.g. semen, sputum, urine, feces, sweat, saliva, nasal mucus, serum, plasma, cerebrospinal fluid, etc., is also possible.

This simple method for the isolation of nucleic acids possesses a large potential for automation, especially in combination with the subject matters of Applications DE-A 41 27 276.5, WO 93/11218, WO 93/11211, and DE-A 41 39 664.2.

EXAMPLE 8
Total Nucleic Acids Preparation from Extremely Small Amounts or Traces of Blood To 1–50 μl of citrate, heparin or EDTA blood, or of frozen and rethawed blood, or of blood renatured from dried traces in textile tissues contained in a 1.5 ml PPN tube are added 1–50 μl of a 4–8 M solution of a chaotropic salt (guanidine hydrochloride, guanidine isothiocyanate, potassium iodide), optionally an organic solvent (phenol, chloroform, ether), and a 1–1000 detergent (NP40; Tween 20, Triton X-100, SDS, CTAB). Then, 1–200 μg of a protease is added, and the mixture is incubated for 1 min at 70° C. or for a longer period of time at lower temperatures (e.g. for 10 min at room temperature).

In this step, efficient lysis of all eukaryotic and/or prokaryotic cells and/or viruses (with concomitant inactivation of infective pathogens) and denaturing and enzymatic degrading of proteins (with concomitant removal of the proteins bound to the nucleic acids) are taking place simultaneously. Adding ½ of volume of a 95–100% alcohol (methanol, ethanol, n-propanol, isopropanol, secondary and tertiary, short-chain or long-chain alcohols) or of organic polymers (PEG) provides highly specific binding conditions for nucleic acids, and the lysate thus adjusted is transferred to the device. Then, the lysate is passed through the membrane or gel matrix by centrifuging or applying pressure, with reversible binding of the nucleic acids to the membrane fibers or gel particles. Impurities, such as proteins, heme, heparin, iron ions, metabolites, etc., are washed out with 0.7 ml of 100 mM NaCl, 10 mM tris/HCl, pH 7.5, 30–80% of a pure alcohol (methanol, ethanol, n-propanol, isopropanol, PEG, secondary and tertiary, short-chain or long-chain alcohols) or a mixture of alcohols. DNA is eluted either with a buffer with low concentration of salts (10 mM tris/HCl, pH 9.0) or with destilled (deionized) water. The advantage of such elution procedures is that the DNA thus obtained may be directly used in subsequent reactions, especially PCR, without further precipitation or buffer-exchange steps.

This method is also useful for the preparation of nucleic acids from extremely small amounts of other body fluids (semen, sputum, urine, feces, sweat, saliva, nasal mucus, serum, plasma, cerebrospinal fluid, etc.) or dried traces thereof.

This simple method for the isolation of nucleic acids possesses a large potential for automation, especially in combination with the subject matters of Applications DE-A 41 27 276.5, WO 93/11218, WO 93/11211, and DE-A 41 39 664.2.

EXAMPLE 9
Total Nucleic Acids Preparation from Tissues

To 100 μg to 10 mg of a tissue in a PPN tube are added a 4–8 M solution of a chaotropic salt (guanidine hydrochloride, guanidine isothiocyanate, potassium iodide), optionally an organic solvent (phenol, chloroform, ether), and a 5–100% detergent (NP40; Tween 20, Triton X-100, SDS, CTAB), and the whole is homogenized by means of a commercially available homogenizer or by mortarpounding in liquid nitrogen. Then, 100–1000 μg of a protease is added, and the mixture is incubated for 10–20 min at 70° C. or for a longer period of time at lower temperatures (e.g. for 30–60 min at room temperature). In this step, efficient lysis of all eukaryotic and/or prokaryotic cells and/or viruses (with concomitant inactivation of infective pathogens) and denaturing and enzymatic degrading of proteins (with concomitant removal of the proteins bound to the nucleic acids) are taking place simultaneously. Adding ½ of volume of a 95–100% alcohol (methanol, ethanol, n-propanol, isopropanol, PEG, secondary and tertiary, short-chain or long-chain alcohols) provides highly specific binding conditions for nucleic acids, and the lysate thus adjusted is transferred to the device. Then, the lysate is passed through the membrane or gel matrix by centrifuging or applying pressure, with reversible binding of the nucleic acids to the membrane fibers or gel particles. Impurities, such as proteins, heme, heparin, iron ions, metabolites, etc., are washed out with 0.7 ml of 100 mM NaCl, 10 mM tris/HCl, pH 7.5, 30–80% of a pure alcohol (methanol, ethanol, n-propanol, isopropanol, PEG, secondary and tertiary, short-chain or long-chain alcohols) or a mixture of alcohols. DNA is eluted either with a buffer with low concentration of salts (10 mM tris/HCl, pH 9.0) or with destilled (deionized)

water. The advantage of such elution procedures is that the DNA thus obtained may be directly used in subsequent reactions, especially PCR, without further precipitation or buffer-exchange steps.

This simple method for the isolation of nucleic acids will function reproducibly from all tissues including tumors, inter alia, and possesses a large potential for automation, especially in combination with the subject matters of Applications DE-A 41 27 276.5, WO 93/11218, WO 93/11211, and DE-A 41 39 664.2 of the same applicant.

EXAMPLE 10
Purification of DNA Fragments from Agarose Gels

A DNA fragment is separated in an agarose gel (TAE or TBE 0.5–2%). The DNA fragment to be isolated is cut out of the gel and mixed with 300 μl of QX1 buffer (7 M $NaPO_4$, 10 mM NaAc, pH 5.3) in a 1.5 ml Eppendorf vessel. After incubation for 10 minutes at 50° C., the agarose will have dissolved. This solution is placed on a centrifuge chromatographic column according to example 1 and centrifuged through. Then, the centrifuge chromatographic column is washed salt-free by centrifuging of 80% ethanol/water through the column and subsequently is centrifuged for 1 min to completely remove excess ethanol. For elution, 0.05 ml of elution buffer (10 mM tris/HCl, pH 8.5) are placed on the chromatographic column and centrifuged through.

EXAMPLE 11
Purification of DNA Fragments from Polyacrylamide (PAA) Gels

The DNA fragment to be isolated is cut out of the PAA gel and transferred to a 2 ml Eppendorf vessel, the gel is crushed and mixed with 500 μl of PAA elution buffer (500 mM $NH_4Ac$, 100 mM $MgAc_2$, 1 mM EDTA, 0.1% SDS). The mixture is incubated for 30 min at 50° C. and then, after addition of 300 μl of QX1 buffer, is centrifuged through a centrifuge chromatographic column. Then, the centrifuge chromatographic column is washed salt-free with 80% ethanol/water and subsequently is centrifuged for 1 min to completely remove excess ethanol. For elution, 0.1 ml of elution buffer (10 mM tris/HCl, pH 8.5) are placed on the chromatographic column and centrifuged through.

EXAMPLE 12
Purification of Large (>3,000 bp) PCR Fragments

A 100 μl PCR amplification reaction is mixed with 500 μl of QXB buffer (5 M GuHCl); preliminary separation of the paraffin oil layer covering the reaction mixture is not necessary. Further purification is performed as in example 4.

EXAMPLE 13
Purification of Single-stranded PCR Products

A 100 μl amplification mixture of an asymmetrical PCR is mixed with 500 μl of PB buffer (5 M GuHCl, 30% isopropanol). Further purification is performed as in example 4. For elution, 0.05 ml of elution buffer (10 mM tris/HCl, pH 8.5) are placed on the chromatographic column and centrifuged through. The eluate will contain about 90% of the single-stranded PCR product which may directly be used for the second amplification of for sequencing.

EXAMPLE 14
Total Nucleic Acids Preparation from Tissues or Cells

Up to 50 mg of a tissue or up to $10^6$ cells are homogenized in 400 μl of a buffered chaotropic solution (4 M GTC, 25 mM sodium citrate, pH 7.5, 2% 2-mercaptoethanol), optionally mixed with a 5–100% detergent (NP40, Tween 20, Triton-X-100, SDS, CTAB, Sarkosyl). In this step, efficient lysis of all eukaryotic and/or prokaryotic cells and/or viruses (with concomitant inactivation of infective pathogens) and denaturing of proteins (especially ribonucleases; with concomitant removal of the proteins bound to the nucleic acids) are taking place simultaneously. Adding 260 μl of a 100% alcohol (methanol, ethanol, n-propanol, isopropanol) provides highly specific binding conditions for nucleic acids. The lysate thus adjusted is transferred to the device.

Subsequently, impurities such as proteins, heme, heparin, metabolites and polysaccharides are washed out with 700 μl of a washing buffer consisting of 1 M GTC, 25 mM tris/HCl, pH 7.5, 400% of an alcohol (methanol, ethanol, n-propanol, isopropanol) and with 700 μl of a washing buffer consisting of 10 mM tris/HCl, pH 7.5, 80% of an alcohol (methanol, ethanol, n-propanol, isopropanol). The nucleic acids are eluted either with a buffer with low concentration of salts (10 mM tris, pH 7.5) or with destined (deionized) water.

What is claimed is:

1. A method for the purification and separation of a nucleic acid mixture by chromatography, comprising the steps of:
   a) adsorbing on a substrate the nucleic acid mixture from an aqueous adsorption solution containing (i) salts effecting a high ionic strength and (ii) 1 to 50% by volume of at least one $C_1$–$C_5$ aliphatic alcohol or polyethylene glycol or at least one $C_1$–$C_5$ aliphatic alcohol and polyethylene glycol wherein said substrate comprises a porous or non-porous mineral substrate selected from the group consisting of silica gel, glass fibers, quartz fibers, and zeolites, followed by
   b) optionally washing said substrate with a washing solution; followed by
   c) eluting said nucleic acid mixture with a solution having a lower ionic strength than the aqueous adsorption solution, effecting thereby a nucleic-acid fraction; and
   d) collecting the nucleic-acid fraction.

2. The method according to claim 1, wherein the salts in the adsorption solution are chaotropic salts in concentrations of from 1 to 8 M.

3. The method of claim 2, wherein the claotropic salts are selected from the group consisting of sodium perchlorate, guanidine hydrochloride, guanidine isothiocyanate, and sodium iodine.

4. The method according to claim 1, wherein the salts are present in the adsorption solution at a concentration of 1 to 10 M and are selected from the group consisting of lithium chloride, sodium chloride, potassium chloride, sodium acetate, urea, and mixtures thereof.

5. The method according to claim 1, wherein the mineral substrate has a particle size of 0.1 μm to 1,000 μm.

6. The method according to claim 1, wherein the substrate is porous, having pore sizes of 2 to 1,000 nm.

7. The method according to claim 1, wherein said porous or non-porous substrate is present in the form of loose fillings.

8. The method according to claim 7, wherein said substrate is comprised of zeolites.

9. The method according to claim 1, wherein said porous or non-porous substrate is present in the form of (i) filter layers of glass fibers or quartz fibers, (ii) a membrane in which silica gel is incorporated, (iii) fibers of quartz, or (iv) glass wool.

10. The method according to claim 9, wherein said substrate is comprised of zeolites.

11. The method according to claim 1, wherein said nucleic acids to be separated and purified are derived from cell cultures, tissues, body fluids, feces, or microorganisms.

12. The method according to claim 11, wherein said nucleic acids to be separated and purified are derived from bacteria or viruses.

13. The method according to claim 11, wherein said nucleic acids to be separated and purified are derived from mycobacterium tuberculosis, cytomegalo-virus, HIV, hepatitis B, hepatitis C, or hepatitis viruses.

14. The method according to claim 11, wherein said nucleic acids to be separated and purified are obtained by polymnerase chain reaction (PCR).

15. The method according to claim 11, wherein said nucleic acids to be separated and purified are plasmid DNA, genomic DNA, or RNA.

16. The method according to claim 11, wherein said nucleic acids to be separated and purified are plasmid DNA, chromosomal, DNA, or RNA from microorganisms.

17. The method according to claim 11, wherein said nucleic acids to be separated and purified are obtained from sequence analyses.

18. The method according to claim 1, wherein after fractionating less than 10% of said nucleic acids are shorter than 10 kb.

19. The method according to claim 1, wherein said nucleic acids are oligonucleotides.

20. The method according to claim 1, wherein the substrate is a membrane of silica gel, and the method further comprises, before the adsorbing step, the steps of:

lysing a cell sample containing the nucleic acids; followed by adjusting conditions for adsorption on the silica gel in one single step.

21. The method according to claim 1, wherein said nucleic acids are plasmids, and lysing the cell sample is by alkaline lysis.

22. The method according to claim 21, wherein the adsorbing step is performed in the presence of detergents.

23. The method according to claim 1, further comprising, after said collecting step, file step of modifying the nucleic acids.

* * * * *